United States Patent
Clements-Macak et al.

(10) Patent No.: US 6,500,666 B1
(45) Date of Patent: Dec. 31, 2002

(54) HYBRIDIZATION OVEN/INCUBATOR ROTISSERIE AND BOTTLE RETAINER SYSTEM

(75) Inventors: Jean Clements-Macak, Seattle, WA (US); Christopher M. Stygar, Pittsburgh, PA (US); William Boehmer, Clairton, PA (US); Robert D. Parks, Pittsburgh, PA (US)

(73) Assignee: Fisher Scientific Company L.L.C., Pittsburgh, PA (US)

( * ) Notice: Subject to any disclaimer, the term of this patent is extended or adjusted under 35 U.S.C. 154(b) by 69 days.

(21) Appl. No.: 09/629,687

(22) Filed: Aug. 1, 2000

(51) Int. Cl.[7] ................................. C12M 1/02
(52) U.S. Cl. ................. 435/303.3; 435/287.2; 435/298.2; 435/809; 422/104; 366/214; 211/74; 211/77; 248/222.11
(58) Field of Search ............................. 435/286.1, 286.2, 435/286.6, 286.7, 287.2, 287.3, 303.1, 809, 303.3; 422/104; 366/214; 211/74, 77; 248/222.11; 24/593.1, 593.11, 594.1

(56) References Cited

U.S. PATENT DOCUMENTS

| | | | | |
|---|---|---|---|---|
| 66,273 A | * | 7/1867 | Wurzbach et al. | 24/593.1 |
| 716,713 A | * | 12/1902 | Hughes | 131/241 |
| 2,494,881 A | * | 1/1950 | Kost | 248/223.41 |
| 3,163,404 A | * | 12/1964 | Kraft et al. | 366/214 |
| 3,320,929 A | * | 5/1967 | Kay | 119/475 |
| 3,747,900 A | * | 7/1973 | Dilts | 366/214 |
| 3,797,792 A | * | 3/1974 | Huber | 248/125.1 |
| 5,380,662 A | * | 1/1995 | Robbins et al. | 366/214 |
| 5,635,398 A | * | 6/1997 | Kapka et al. | 366/197 |
| 5,918,979 A | * | 7/1999 | Martin et al. | 366/211 |

\* cited by examiner

Primary Examiner—William H. Beisner
(74) Attorney, Agent, or Firm—Rader, Fishman & Grauer PLLC (57) ABSTRACT

The invention relates to a hybridization oven or incubator, and more particularly to a rotisserie and carousel/retainer system for use therein. The rotisserie includes a spindle that is readily removable from the oven, having a first end received in an annular bracket and a second end received annular bracket with an upper slot for passage of the spindle into the bracket. The carousel clip system includes a thin metal carousel plate preferably formed of a stainless steel and having a plurality of ears bent perpendicular to the carousel plate and having a detent aperture therein. A plurality of bottle retainers are removably attached to the carousel plate, the retainers having a base channel adapted to receive the ears of the carousel plate and further including a resilient arm having a detent projecting into the channel and deflectable during insertion of the ear into the channel, the detent entering the detent aperture of the ear under the bias of the resilient arm to removably retain the clip on the ear of the carousel plate.

12 Claims, 7 Drawing Sheets

HYBRIDIZATION OVEN/INCUBATOR ROTISSERIE AND BOTTLE RETAINER SYSTEM

BACKGROUND OF THE INVENTION

1. Field of the Invention

The invention relates to a rotisserie for use in an incubator or hybridization oven. In one of its aspects, the invention relates to bottle retainers for attachment to the rotisserie. In another of its aspects, the invention relates to a structure for attaching the bottle retainers to a carousel of the rotisserie. In a further aspect, the invention relates to a structure for mounting and removing the rotisserie from the incubator or hybridization oven.

2. Description of the Related Art

Hybridization ovens, or incubators, including a rotisserie mechanism are well known in the art. An example of a rotisserie mechanism in an incubator is disclosed in U.S. Pat. No. 5,380,662 to Robbins et al. The rotisserie mechanism is a chain driven spindle with eccentrically mounted wheels carrying a plurality of clips secured to the wheels by fasteners. The clips are formed of stainless steel or anodized aluminum, and have resilient arms for releasably holding sample bottles within the incubator as the rotisserie rotates.

There are a number of problems with the prior art metal clips. One problem is that the metal edges are often sharp. As a result, when sample bottles are either placed or removed from the metallic clips, lab gloves have a tendency to rip or tear as they rub against the sharp edges.

Another problem is that sample bottles come in different sizes and are used in different combinations as the application dictates. Therefore, the incubator must be adaptable to different bottles; different sizes of bottles will generally require different clips to securely hold them without breaking them. In the Robbins et al. '662 incubator, the clips are not adaptable to a wide range of bottle sizes, nor are they easily removable from the rotisserie mechanism. As a result, use of the incubator for different sizes or combinations of sample bottles requires modification or replacement of the rotisserie.

A third problem results even when sample bottles of the same size are used. Over time, the clips have the tendency to lose their capability to retain sample bottles as springiness/biasing capabilities are reduced through use.

It would be advantageous to have a rotisserie mechanism that provided for ready substitution or replacement of the rotisserie within the oven, or, preferably, ready substitution of the clips carried by the rotisserie. Such a rotisserie mechanism would lack sharp edges, be readily adaptable to sample bottles of different sizes, and to different combinations of sample bottles.

SUMMARY OF THE INVENTION

The invention relates to a rotisserie assembly for carrying fluid-containing receptacles along a generally circular path about an axis of rotation, comprising a spindle extending along the axis of rotation, at least one generally circular carousel mounted on the spindle, at least one bottle retainer comprising a bottle retainer base mounting a pair of spaced resilient arms and defining a retainer for a fluid-containing receptacle of a first size, and a detent mechanism mounted between the bottle retainer base and the carousel for removably mounting the bottle retainer to the carousel between a first attached position and a second detached position. The clip is formed from a non-metallic material with non-sharp edges to avoid potential ripping or tearing to lab gloves as sample bottles are inserted and removed from the rotisserie. In a preferred embodiment the clips are formed from a flame-retardant fiberglass reinforced nylon 6/6 material sold under the trade name RTP 201 FR, having the ability to withstand temperatures of 60 degrees Celsius for prolonged periods and up to 110 degrees Celsius and higher for brief periods of time without losing their ability to provide appropriate biasing to hold the sample bottles in a secure orientation.

Another embodiment of the invention comprises a plurality of bottle retainers in a selection of sizes, each bottle retainer comprising a base and a pair of resilient arms defining a retainer for a fluid-containing receptacle, wherein the resilient arms of each bottle retainer are configured to retain a fluid-containing receptacle of one of a number of different sizes, and wherein the bottle retainers are adapted to be removably mounted to the carousel.

The invention is further directed to the bottle retainer, comprising a base portion and opposing arcuate resilient arms connected to the base portion, wherein the base portion has at least one of a socket and a clip and the carousel has the other of the socket and the clip, the socket and clips adapted to selectively engage one another in a removable fashion. One of the socket and clip has a detent adapted to engage a shoulder of the other of the socket and clip, whereby the selective removal of the clip from the socket is accomplished by disengaging the detent from the shoulder.

DESCRIPTION OF THE PREFERRED EMBODIMENT

Figure 1:
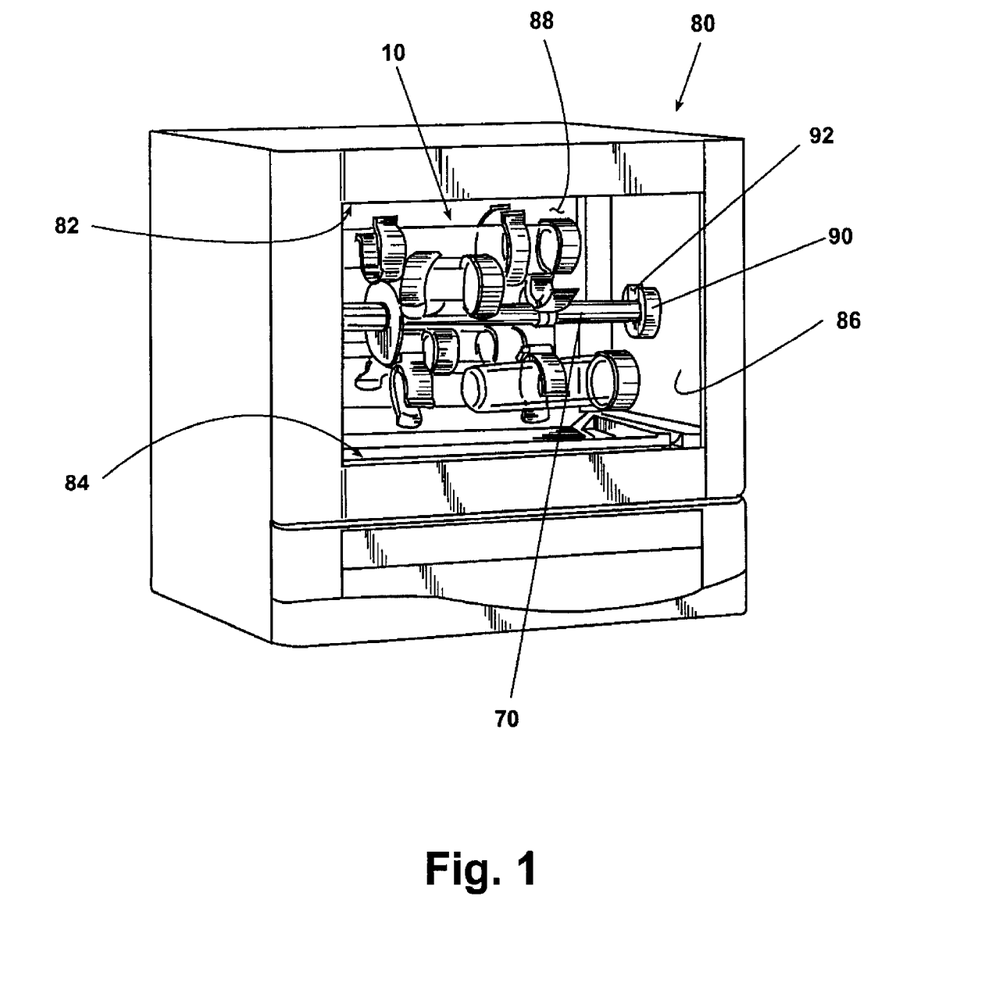
FIG. 1 is a perspective view of a hybridization oven with removable rotisserie and bottle retainer system according to the invention.

Referring to FIG. 1, a hybridization oven/incubator 80 includes an upper wall 82, lower wall 84 and opposing side walls 86 defining an oven cavity 88. Incubator 80 also includes a door (not shown for clarity) for sealing a front side of cavity 88 during use. Incubator 80 further includes a plurality of retainers 90 mounted on side walls 86 of cavity 88 for rotatably holding a spindle 70 of a rotisserie and bottle retainer system 10. A first annular retainer (not shown) includes a central aperture for receiving a first end of spindle 70. Second retainer 90 is substantially annular, and includes a slot 92 joining a central aperture to the edge of the retainer, the slot 92 being directed upwardly to receive the second end of the spindle 70 so that spindle 70 is rotatably supported by second retainer 90. A drive mechanism (not shown) and an end of spindle 70 are configured for operable engagement, the drive mechanism engaging an end of spindle 70 at one of the first and second retainers 90 for imparting rotation to spindle 70 about its longitudinal axis.

Figure 2:
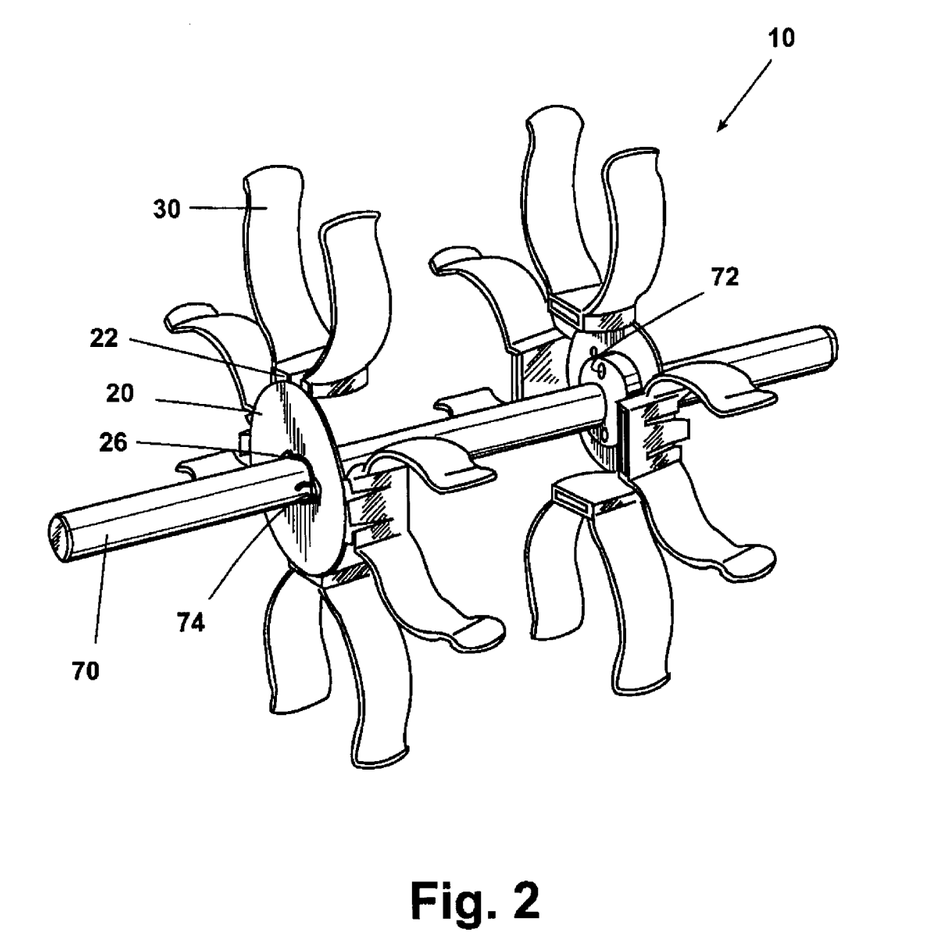
FIG. 2 is a perspective view of the rotisserie and bottle retainer system of FIG.
Figure 3:
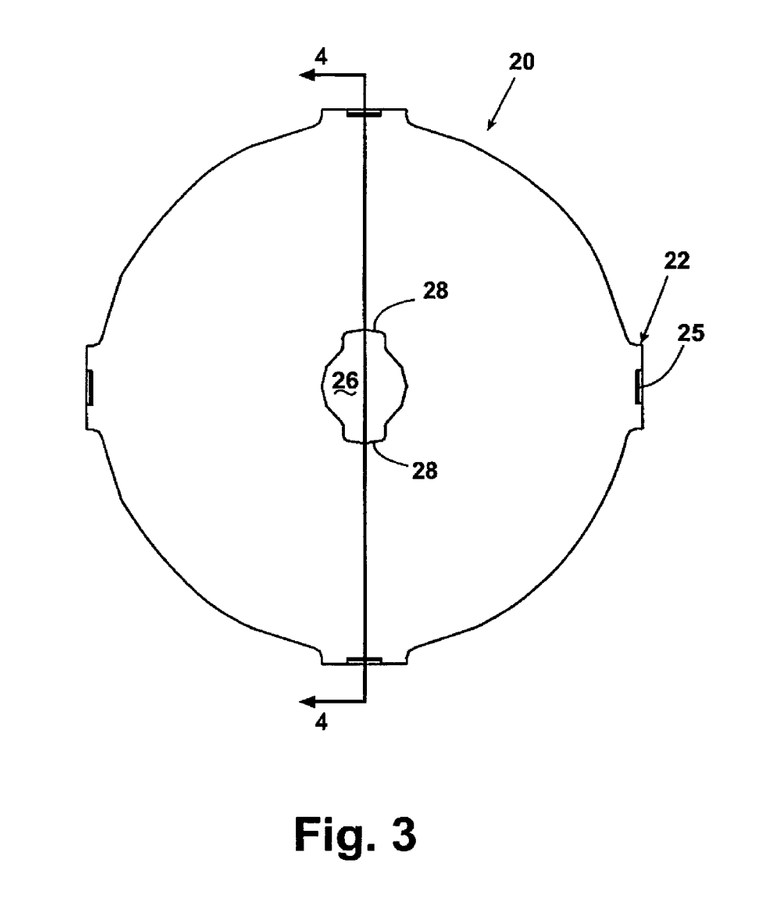
FIG. 3 is a plan view of a carousel plate of the rotisserie and bottle retainer system of FIGS. 1 and 2.
Figure 4:
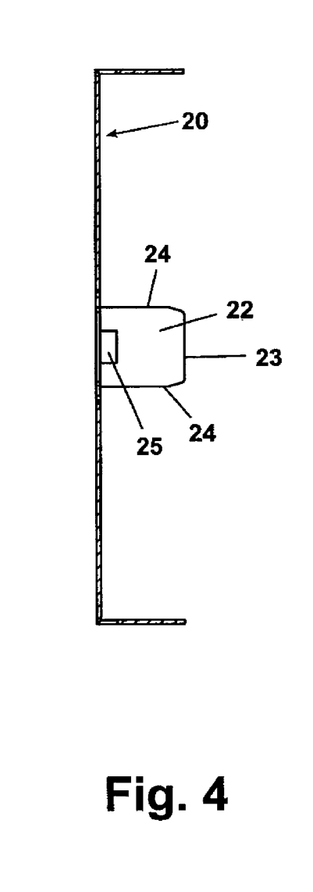
FIG. 4 is a cross-sectional view taken through line 4—4 of FIG. 3.

Referring now to FIGS. 2–4, rotisserie and bottle retainer system 10 includes spindle 70 and at least one carousel bracket 72 non-rotatably attached to spindle 70 in the manner of a collar. Carousel bracket 72 includes resilient, outwardly biased bracket prongs 74 projecting from bracket 72 generally parallel to spindle 70.

A carousel plate 20 is secured to an adjacent carousel bracket 72. Carousel plate 20 has a generally flat and circular central portion including a central aperture 26 through which spindle 70 extends. Carousel plate 20 is formed of a sheet metal material, such as stainless steel, approximately 0.05 inches thick, to provide sufficient rigidity and strength. It further comprises a plurality of ears 22 integrally formed at an outer periphery of the central portion and bent substantially perpendicularly to plate 20, each for carrying a bottle retainer 30. In the disclosed embodiment, the ears act as clips detachably received in a corresponding socket defined by a bottle retainer as discussed further below. Alternatively, however, the ears may define a socket receiving a mating clip associated with the bottle retainer 30. When acting as clips, ears 22 each have an end 23 distal from carousel plate 20 and parallel thereto and sides 24 perpendicular to plate 20 and separated from each other to give ear 22 a predetermined width. Ears 22 further comprise an aperture 25 extending from plate 20 to a predetermined depth from end 23 of ear 22.

Carousel plate aperture 26 further includes retention wings 28 that preferably removably engage bracket prongs 74 to provide a drive connection between carousel 20 and carousel bracket 72 that is resistant against slippage. In practice, bracket prongs 74 are aligned with wings 28 of aperture 26, and flex inwardly as they pass through wings 28. As plate 20 abuts bracket 72, prongs 74 bias outwardly, thereby non-rotatably securing plate 20 to bracket 72, and thus to spindle 70.

Referring now to FIGS. 5–8, bottle retainer 30 is comprised of a base portion 32, being generally rectangular in a cross section, and a pair of arcuate resilient arms 50 extending upwardly from the base in an opposing fashion in the form of a "U." The edges of arms 50 are purposely non-sharp or dull to avoid potential tears or rips to laboratory gloves and the like when sample bottles are inserted or removed from retainers 30. It is easier to form the desired edges with a non-metallic material.

Bottle retainer 30 is integrally molded from a resilient polymer, preferably injection molded. In a preferred embodiment retainers 30 are formed from a flame-retardant fiberglass nylon 6/6 material sold under the trade name RTP 201 FR from RTP Company of Winona, Minn. The material has a reported "Deflection Temperature" or HDT (per ASTM D-648) of 204 degrees Celsius at 264 psi. In testing, the retainers 30 formed from the preferred material have the ability to withstand the specified maximum operating temperature of 85 degrees Celsius for prolonged periods and up to higher temperatures for brief periods of time without losing dimensional stability and the like that could adversely affect their ability to provide appropriate biasing to hold the sample bottles in a secure orientation. One such test was conducted at 110 degrees Celsius. Thus, RTP 201 FR has been found to be a conservative choice for retainers 30.

Figure 6:
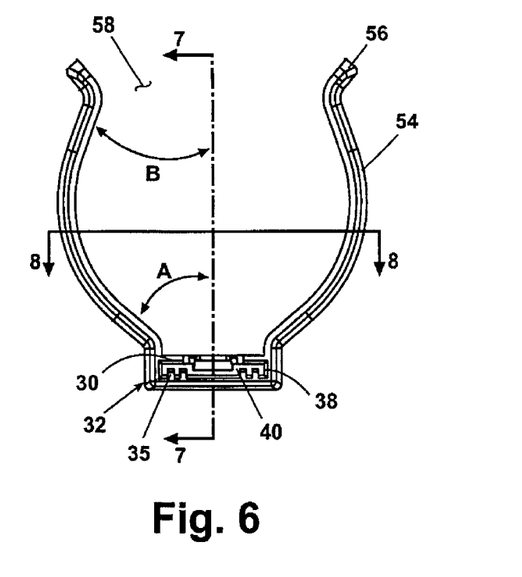
FIG. 6 is an elevation of the bottle retainer of FIG. 5.
Figure 7:
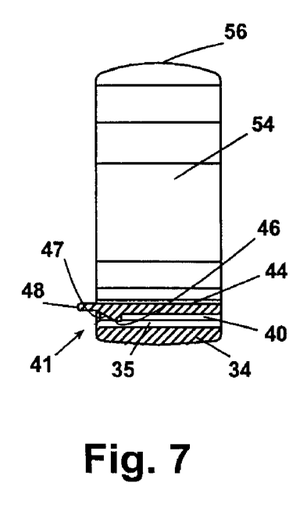
FIG. 7 is a cross-sectional view taken through line 7—7 of FIG. 6.
Figure 8:
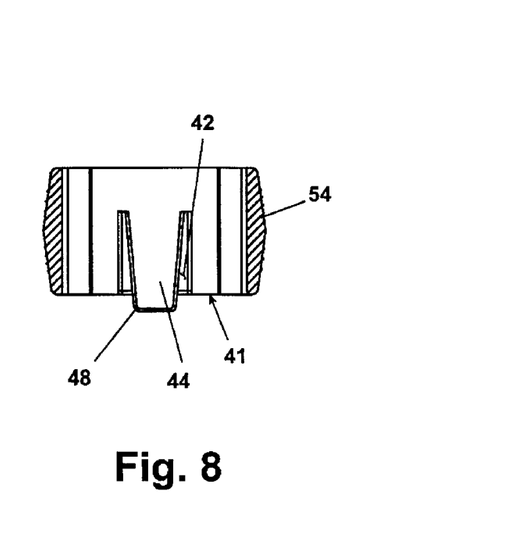
FIG. 8 is a cross-sectional view taken through line 8—8 of FIG. 6.
Figure 9:
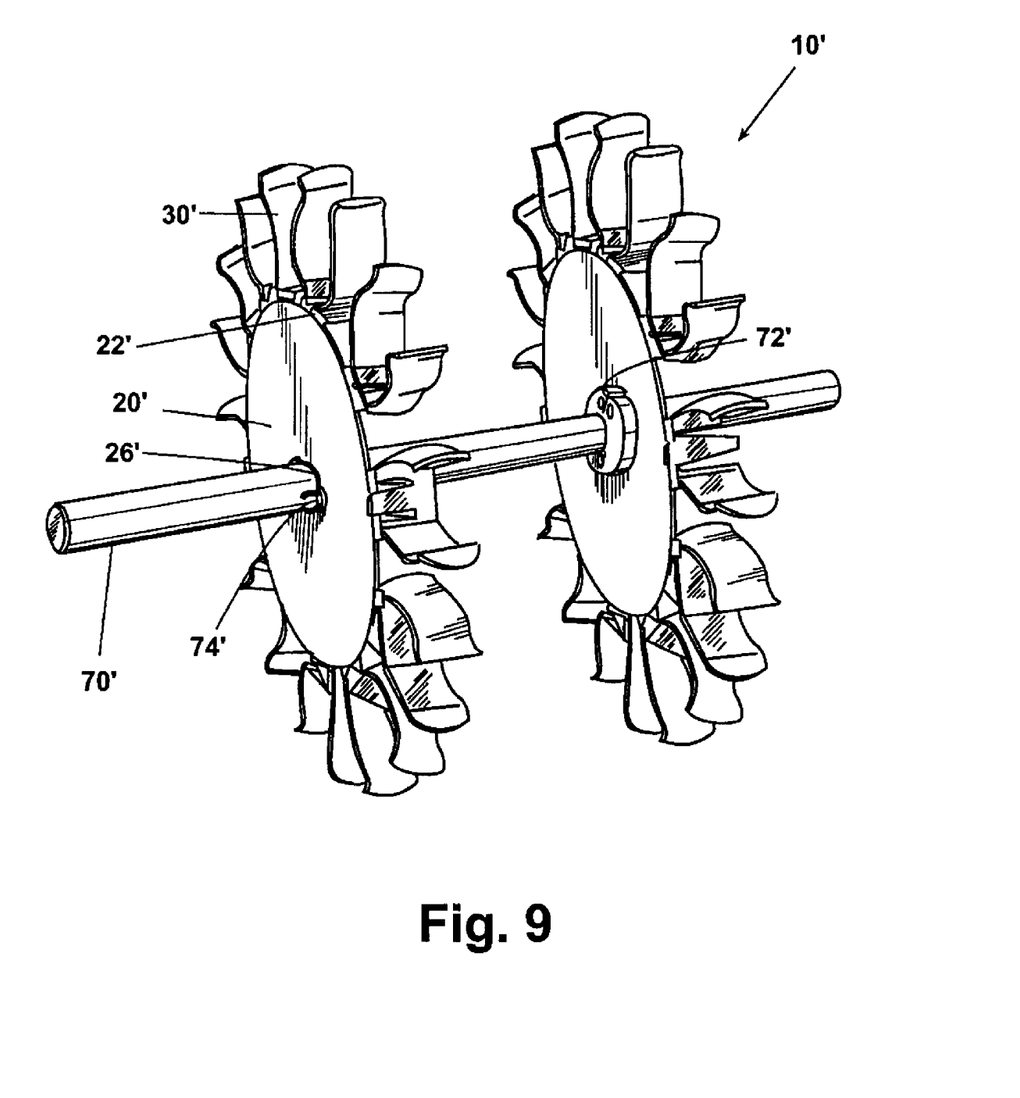
FIG. 9 is a perspective view of another embodiment of the rotisserie and bottle retainer system according to the invention.
Figure 10:
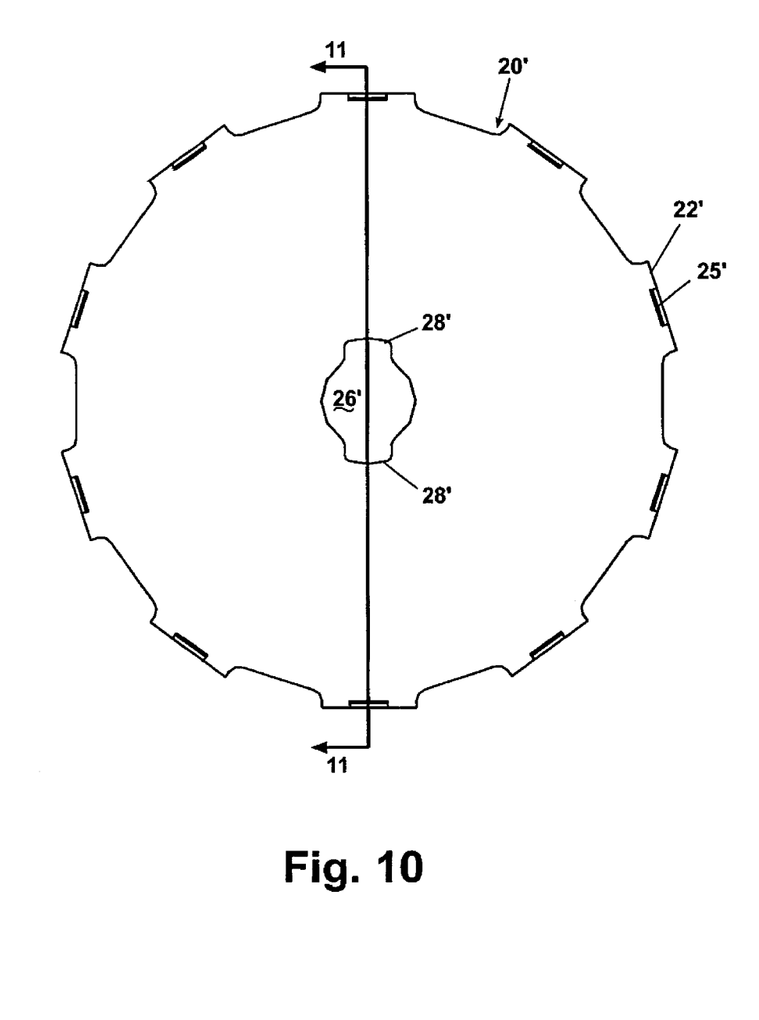
FIG. 10 is a plan view of a carousel plate of the rotisserie and bottle retainer system of FIG. 9.
Figure 11:
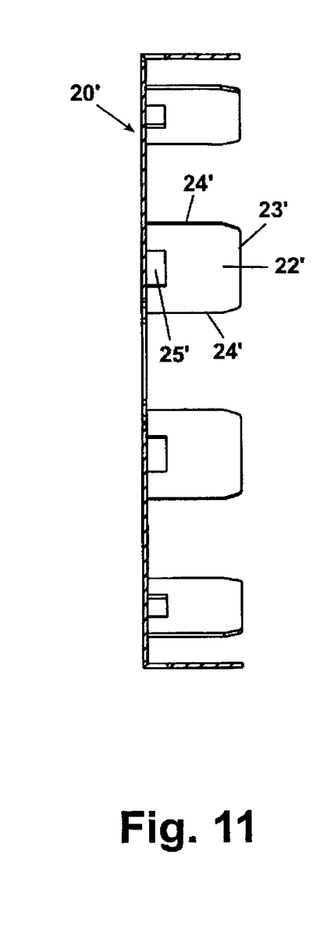
FIG. 11 is a cross-sectional view taken through line 11—11 of FIG. 10.
Figure 12:
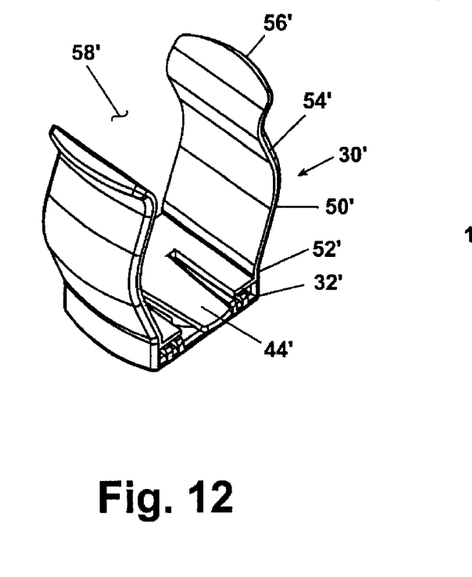
FIG. 12 is a perspective view of a bottle retainer of the rotisserie and bottle retainer system of FIGS. 9–11.
Figure 13:
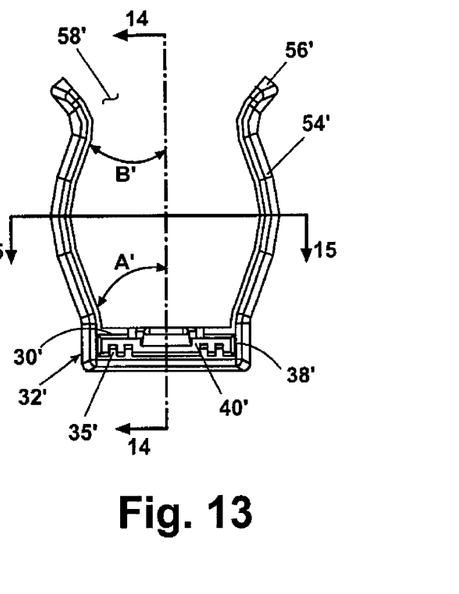
FIG. 13 is an elevation of the bottle retainer of FIG. 12.
Figure 14:
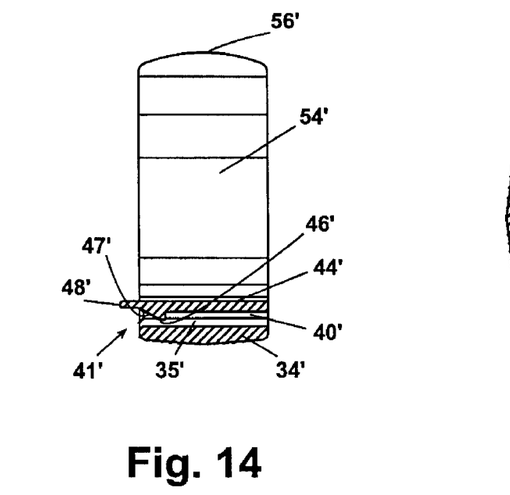
FIG. 14 is a cross-sectional view taken through line 14—14 of FIG. 13.
Figure 15:
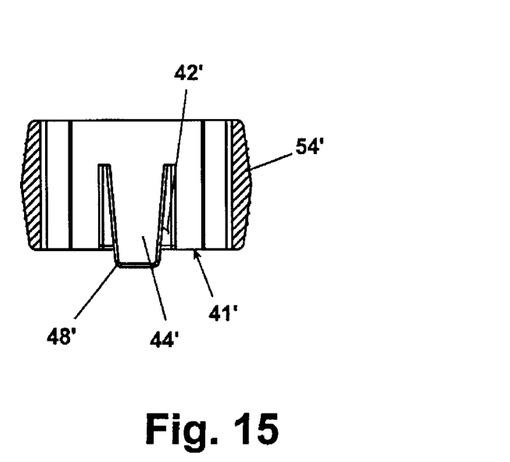
FIG. 15 is a cross-sectional view taken through line 15—15 of FIG. 13.

Base portion 32 includes a bottom wall 34 and a top wall 36 in parallel relationship to one another and joined by side walls 38. Walls 34, 36, 38 define a channel 40 that is generally rectangular in cross section, and further includes a number of upstanding ribs 35 projecting from bottom wall 34 to effectively reduce the clear height of channel 40. Top wall 36 includes two partial depth slots 42, best seen in FIG. 8, the portion of top wall 36 between slots 42 forming a resilient tongue 44. As shown in FIGS. 7 and 8, resilient tongue 44 extends beyond a channel first end 41 to form a release tab 48. Resilient tongue 44 further includes a detent 46, best seen in FIG. 7, that projects into channel 40, and a ramped face 47 increasing the thickness of resilient tongue 44 from channel first end 41 to detent 46. As can be seen in FIGS. 6 and 7, detent 46 extends below the level of the top of ribs 35.

Figure 5:
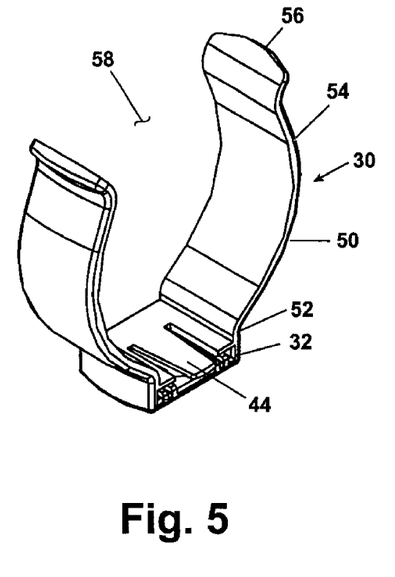
FIG. 5 is a perspective view of a bottle retainer of the rotisserie and bottle retainer system of FIGS. 1–4.

Resilient arms 50 each have a first end 52 proximal to base 32, extending perpendicularly at base 32 then curving outwardly until attaining a displacement angle A from a centerline of retainer 30 of approximately 50 degrees. The curvature of arms 50 then reverses as first ends 52 join arcuate portions 54 of resilient arms 50, arcuate portions 54 being configured and of such a radius to conform to a bottle of the size intended to be carried by a given retainer 30. Arcuate portions 54 are generally extended about the centerline of the retainer 30 until they define an angle B of approximately 20 degrees with respect to the centerline of retainer 30. Resilient arms 50 each reverse curvature again at divergent ends 56 away from the center line of retainer 30. Divergent ends 56 of resilient arms 50 define a clip opening 58 therebetween. The divergent nature of ends 56 aids in guiding a bottle into clip opening 58. In the disclosed embodiment angle B is less than angle A to provide a desired biasing to retain a bottle while permitting appropriate flexing of arms 50 so that a bottle may be inserted and released. Further, the rest displacement between the inner periphery of arms 50 is preferably slightly less than the corresponding outer bottle diameter to provide additional biasing retention to the bottle after it is inserted into a retainer 30.

Each retainer 30 is releasably assembled to carousel plate 20 by inserting end 23 of one ear 22 into channel first end 41 of retainer 30, ear sides 24 being slightly tapered at end 23 to aid in insertion. As ear 22 enters channel first end 41, ear end 23 will press against ramped face 47, deflecting resilient tongue 44 and detent 46 out of channel 40 so that ear 22 can enter channel 40 on top of ribs 35. Ribs 35, having a smaller surface area than bottom wall 34, offer less resistance to insertion of ear 22 in channel 40. When ear 22 is fully inserted in channel 40, channel first end 41 abuts carousel plate 20 and detent 46 aligns with ear aperture 25 so that resilient tongue 44 will bias detent 46 into aperture 25. Retainer 30 is thereby fixed to plate 20 in a direction perpendicular to plate 20. Release tab 48 extends beyond first channel 41 and also the face of carousel plate 20, so that should it become necessary or desirable to remove retainer 30 from carousel plate 20, release tab 48 is accessible; the user can press against release tab 48 to deflect resilient tongue 44 away from ear 22, thereby removing detent 46 from aperture 25 and allowing retainer 30 to be displaced away from plate 20 and ear 22 to be removed from channel 40.

FIGS. 9–15 disclose an alternative embodiment of the rotisserie and bottle retainer system according to the invention. In the figures, like elements of the invention carry like numbering of the first disclosed embodiment, modified by a prime (') designation. Carousel plate 20' comprises a greater number of ears 22', each ear 22' having the same dimensional configuration as ear 22 of the first embodiment, and each retainer 30' having a base portion 32' having the same dimensional configuration as base 32 of retainer 30. Thus, retainers 30, 30' are interchangeable and usable on either carousel plate 20, 20', providing the user with greater flexibility in the use of the rotisserie and bottle retainer system within a hybridization oven. For example, a single carousel plate can be configured with clips of varying sizes to carry bottles of varying sizes, or a given carousel plate can be reconfigured entirely to carry bottles of a new and different size, all without the use of tools. Moreover, if a bottle retainer 30 becomes damaged or loses its bottle retention capabilities, it is easily replaced.

FIGS. 12–15 illustrate an alternative embodiment of bottle retainer 30', configured to grasp a bottle of smaller diameter than the bottle to be grasped by bottle retainer 30'. By way of example, retainer 30' differs in configuration from retainer 30 in that resilient arm first end 52', as it curves outwardly from the clip centerline, only reaches a displacement angle A' of approximately 20 degrees before reversing curvature into resilient arm arcuate portion 54'. Angle B' of arcuate portion 54' and divergent ends 56' are generally equivalent to angle B and the divergent end 56 of the first embodiment, as this has been found to be optimal for safely receiving and retaining a bottle in bottle retainer 30, 30'. Each bottle retainer 30, 30' is configured to grasp a bottle of a given size, or within a given range of that size. It is anticipated to configure a plurality of bottle retainers spanning, together, the full range of bottle sizes that are anticipated for use in the incubator and with the rotisserie and bottle retainer system. An appropriate set of bottle retainers, all having a common base configuration, can therefore be used with a common carousel plate or plates to handle the full range of bottle sizes, obviating the need for separate rotisseries, or even separate pre-configured carousel and bottle retainer assemblies.

While the invention has been specifically described in connection with certain specific embodiments thereof, it is to be understood that this is by way of illustration and not of limitation, and the scope of the appended claims should be construed as broadly as the prior art will permit.

What is claimed is:

1. A rotisserie assembly for carrying fluid-containing receptacles along a generally circular path about an axis of rotation, comprising:
   a spindle extending along the axis of rotation;
   at least one generally circular carousel mounted on the spindle;
   at least one bottle retainer comprising a bottle retainer base mounting a pair of spaced resilient arms and defined to selectively engage and retain a fluid containing receptacle of a first size; and
   wherein the carousel includes one of a clip and a socket of a predetermined size and the bottle retainer includes the other of the clip and the socket, the socket including a resilient tongue having a detent that releasably engages a shoulder on the clip to detachably mount the bottle retainer to the carousel.

2. The rotisserie assembly of claim 1, further comprising a plurality of bottle retainers in a selection of sizes, each configured for engaging and retaining a fluid-containing receptacle, wherein the resilient arms are separated by any one of a number of predetermined distances generally less than the corresponding outer dimension of the fluid-containing receptacle before receptacle insertion to provide for a biasing retention.

3. A retainer for holding a bottle to a carousel in a rotisserie assembly of a hybridization oven or incubator, comprising a base portion and opposing resilient arms connected to the base portion, wherein the base portion has at least one of a socket and a clip and the rotisserie has the other of the socket and the clip, and wherein the socket has a resilient tongue that includes a detent adapted to engage a shoulder of the clip, whereby the selective removal of the clip from the socket is accomplished by deflecting the tongue away from the clip to disengage the detent from the shoulder.

4. The retainer of claim 3, wherein the base portion and resilient arms are integrally molded.

5. In an oven of the type having a housing defining a cavity, a door pivotally mounted to the housing for enclosing the cavity, a controlled heat source for developing a temperature within the oven, and a rotisserie, the rotisserie comprising a spindle having a longitudinal axis, a motive mechanism, at least one wheel fixed to the spindle, and at least one bottle retainer comprising a base mounting a pair of spaced resilient arms and defined to selectively engage and retain a fluid-containing receptacle of a first size, wherein the spindle is operably connected to the motive mechanism for developing a rotational motion in the spindle about the longitudinal axis; the improvement comprising:
   a detent mechanism mounted between the bottle retainer and the wheel for removably mounting the bottle retainer to the wheel between a first attached position and a second detached position, the detent mechanism including a clip and a socket, wherein the wheel includes one of the clip and the socket and the bottle retainer includes the other of the clip and the socket, the socket including a resilient tongue having a detent that releasably engages a shoulder on the clip to detachably mount the bottle retainer to the wheel, thereby eliminating the need for a separate tool to removably engage and release the bottle retainer with respect to the wheel.

6. The oven of claim 5, further comprising a plurality of bottle retainers in a selection of sizes, the resilient arms separated in a rest orientation by any one of a number of predetermined distances to selectively engage and retain a fluid-containing receptacle having an outer periphery generally corresponding to or greater than the predetermined distance.

7. A retainer for holding a bottle to a carousel in a rotisserie assembly of a hybridization oven or incubator, comprising a base portion and opposing resilient arms connected to the base portion, wherein the base portion has at least one of a socket and a clip and the rotisserie has the other of the socket and the clip, the socket comprising a lower wall and an upper wall joined by a pair of opposing side walls to define a substantially rectangular closed channel, the walls each having a first end and a second end, the channel having a first end and a second end corresponding to the first and second ends of the walls and a plurality of ribs extending partially into the channel from the lower wall toward the upper wall and from the first end to the second end, and wherein one of the socket and clip has a detent adapted to engage a shoulder of the other of the socket and clip, whereby the clip is selectively removed from the socket by disengaging the detent from the shoulder.

8. A rotisserie assembly for carrying fluid-containing receptacles along a generally circular path about an axis of rotation, comprising:

a spindle extending along the axis of rotation;

at least one generally circular carousel mounted on the spindle;

at least one bottle retainer comprising a bottle retainer base mounting a pair of spaced resilient arms and defined to selectively engage and retain a fluid containing receptacle of a first size; and wherein the carousel includes one of a clip and a socket of a predetermined size and the bottle retainer includes the other of the clip and the socket, the socket includes a lower wall and an upper wall joined by a pair of opposing side walls to define a closed channel, a plurality of ribs extend partially into the channel, and a resilient tongue having a detent that releasably engages a shoulder on the clip to detachably mount the bottle retainer to the carousel.

9. In an oven of the type having a housing defining a cavity, a door pivotally mounted to the housing for enclosing the cavity, a controlled heat source for developing a temperature within the oven, and a rotisserie, the rotisserie comprising a spindle having a longitudinal axis, a motive mechanism, at least one wheel fixed to the spindle, and at least one bottle retainer comprising a base mounting a pair of spaced resilient arms and defined to selectively engage and retain a fluid-containing receptacle of a first size, wherein the spindle is operably connected to the motive mechanism for developing a rotational motion in the spindle about the longitudinal axis; the improvement comprising:

a detent mechanism mounted between the bottle retainer and the wheel for removably mounting the bottle retainer to the wheel between a first attached position and a second detached position, the detent mechanism including a clip and a socket, wherein the wheel includes one of the clip and the socket and the bottle retainer includes the other of the clip and the socket, the socket including a lower wall and an upper wall joined by a pair of opposing side walls to define a closed channel, a plurality of ribs extend partially into the channel, and a resilient tongue having a detent that releasably engages a shoulder on the clip to detachably mount the bottle retainer to the wheel, thereby eliminating the need for a separate tool to removably engage and release the bottle retainer with respect to the wheel.

10. The retainer of claim 9, wherein the upper wall comprises a pair of slots extending partially from the first end toward the second end to define a resilient tongue integrally formed with the upper wall.

11. The retainer of claim 10, wherein the resilient tongue includes a release tab and a detent portion, the release tab extending beyond the first end and the detent portion extending partially into the channel toward the lower wall.

12. The retainer of claim 11, wherein the resilient tongue has an engagement position and a disengagement position, the resilient arm in the engagement position being parallel with the upper wall with the detent portion extending into the channel and in the disengagement position being displaced away from the lower wall with the detent portion not extending into the channel.

* * * * *